United States Patent [19]
Knuth et al.

[11] Patent Number: 5,869,310
[45] Date of Patent: Feb. 9, 1999

[54] ISOLATED AGARASE ENZYME FROM FLAVOBACTERIUM SP. STRAIN NR19, CLONED GENES THEREFOR, AND EXPRESSION THEREOF IN TRANSFORMED HOST CELLS

[75] Inventors: Mark W. Knuth, Waunakee; Kimberly K. Knoche, Middleton; Susanne Selman; James R. Hartnett, both of Madison, all of Wis.

[73] Assignee: Promega Corporation, Madison, Wis.

[21] Appl. No.: 655,704

[22] Filed: Jun. 3, 1996

[51] Int. Cl.$^6$ .............................. C12N 9/38; C12N 9/24; C12N 1/00
[52] U.S. Cl. ........................... 435/207; 435/200; 435/850
[58] Field of Search ............................... 435/69.1, 252.3, 435/320.1, 200, 207, 850

[56] References Cited

U.S. PATENT DOCUMENTS 5,418,156  5/1995  Stosz et al. .............................. 435/200

OTHER PUBLICATIONS

Sugano, Yasushi; Terada, Ichiro; Arita, Masatoshi; Noma, Masana; and Matsumoto, Takashi, Purification and Characterization of a New Agarase from a Marine Bacterium, *Vibrio* sp. Strain JT0107, *Applied and Environmental Microbiology,* (May 1993), pp. 1549–1554.

Sugano, Yasushi; Matsumoto, Takashi; Kodama, Hisashi; and Noma, Masana, Cloning and Sequencing of agaA, a Unique Agarase 0107 Gene from a Marine Bacterium, *Vibrio* sp. Strain JT0107, *Applied and Environmental Microbiology.* (Nov. 1993), pp. 3750–3756.

Sugano, Yasushi; Matsumoto, Takashi; and Noma, Masana, Sequence analysis of the agaB gene encoding a new β–agarase from *Vibrio* sp. strain JT0107, *Biochimica et Biophysica Acta,* (1994), 1218 pp. 105–108.

Aoki, Takahiko; Araki, Toshiyoshi; and Kitamikado, Manabu; Purification and characterization of a novel β–agarase from *Vibrio* sp. AP–2, *Eur. J. Biochem.,* (1990), 187: 461–465.

Carlsson, J., and Malmqvist, M., Effects of Bacterial Agarase on Agarose Gel in Cell Culture, In Vitro, (1977), 13:7: 417–422.

Potin, Philippe; Richard, Christophe; Rochas, Cyrille; and Kloareg, Bernard, Purification and characterization of the α–agarase from *Alteromonas agarlyticus* (Cataldi) comb. nov., strain GJ1B, *Eur. J. Biochem.,* (1993), 214: 599–607.

Young, K.; Hong, K.C.; Duckworth, M.; and Yaphe, W., Enzymic Hydrolysis of Agar and Properties of Bacterial Agarases, *Proc. of the 7th International Seaweed Symp.,* (1971), pp. 469–472.

Leon, Oscar; Quintana, Luis; Peruzzo, Gina; and Slebe, Juan Carlos, Purification and Properties of an Extracellular Agarase from *Altermonas* sp. Strain C–1, *Applied and Environmental Microbiology,* (Dec. 1992), pp. 4060–4063.

Andrykovitch, George and Marx, Irene, Isolation of a New Polysaccharide–Digesting Bacterium from a Salt Marsh, *Applied and Environmental Microbiology,* (Apr. 1988), pp. 1061–1062.

Morrice, Lora M.; McLean, Maitland W.; Long, William F. and Williamson, Frank B., β–Agarases I and II from *Pseudomonas atlantica*–Substrate specificities, *Eur. J. Biochem.* (1983) 137: 149–154.

Morrice, Lora M.; McLean, Maitland W.; Long, William F. and Williamson, Frank B., β–Agarases I and II from *Pseudomonas atlantica*–Purifications and some properties, *Eur. J. Biochem.* (1983) 137: 149–154.

Groleau, D. and Yaphe, W., Enzymatic hydrolysis of agar: purification and characterization of β–neoagarotetraose hydrolase from *Pseudomonas atlantica, Can. J. Microbiol.,* (1977), 23: 672–679.

Belas, Robert; Bartlett, Douglas, and Silverman, Michael, Cloning and Gene Replacement Mutagenesis of a *Pseudomonas atlantica* Agarase Gene, *Applied and Environmental Microbilogy,* (Jan. 1988) 54:1, pp. 30–37.

Belas, Robert, Sequence Analysis of the agrA Gene Encoding β–Agarase from *Pseudomonas atlantica, Journal of Bacteriology,* (Jan. 1989) pp. 602–605.

Malmqvist, Magnus, Purification and Characterization of Two Different Agarose–Degrading Enzymes, *Biochimica et Biophysica Acta,* (1978), 537: pp. 31–43.

Yamaura, Izumi; Matsumoto, Toshihiko; Funatsu, Masaru; Shigeiri, Hisaji and Shibata, Teruhiko, Purification and Some Properties of Agarase from *Pseudomonas* sp. PT–5, *Agric. Biol. Chem.,* (1991) 55(10): pp. 2531–2536.

Bibb, Mervyn J.; Jones, George H.; Joseph, Richard; Buttner, Mark J. and Ward, Judy M., The Agarase Gene (dagA) of *Streptomyces coelicolor* A3(2): Affinity Purification and Characterization of the Cloned Gene Product, *Journal of General Microbiology,* (1987), 133: pp. 2089–2096.

Buttner, Mark J.; Fearnley, Ian M. and Bibb, Mervyn J., The agarase gene (dagA) of *Streptomyces coelicolor* A3(2): nucleotide sequence and transcriptional analysis, *Mol Gen Genet,* (1987), 209: pp. 101–109.

Usov, A.I. and Miroshnikova, L.I., Isolation of agarase from *Littorina mandshurica* by affinity chromatography on Biogel A, *Carbohydrate Research,* (1973), 43: pp. 204–207.

Gudz, S.P.; Matviiko, S.G. and Dumych, M.F., A New Species of Agarlytic Soil Bacteria of the Genus, *Microbiologiya,* (1986) 55(2): pp. 248–252.

(List continued on next page.)

*Primary Examiner*—Rebecca E. Prouty
*Assistant Examiner*—Elizabelli Slobodyansky
*Attorney, Agent, or Firm*—DeWitt Ross & Stevens S.C.

[57] ABSTRACT

Novel purified agarase enzymes from Flavobacterium sp. strain NR19 and cloned genes encoding the agarase enzymes are disclosed. Transformed host cells which express the novel agarase enzymes in isolatable quantities are also described. Also disclosed are antibodies specifically reactive with the novel agarases.

3 Claims, 6 Drawing Sheets

OTHER PUBLICATIONS

Zobell, Claude E. and Allen, Esther C., The Significance of Marine Bacteria in the Fouling of Submerged Surfaces, *J. Bacteriol.*, (1934), 29: pp. 239–251.

van der Meulen, H.J.; Harder, W. and Veldkamp, H., Isolation and characterization of *Cytophaga flevensis* sp. nov., a new agarolytic flexibacterium, *Antonie van Leeuwenhoek*, (1974), 40: pp. 329–346.

van der Meulen and Harder, W., Production and characterization of the agarse of *Cytophaga flevensis*, *Antonie van Leeuwenhoek*, (1975), 41: pp. 431–447.

van der Meulen, H.J. and Harder, W., Characterization of the neoagarotetra–ase and neoagarobiase of *Cytophaga flevensis*, *Antonie van Leeuwenhoek*, (1976), 42: pp. 81–94.

Duckworth, M. and Turvey, J.R., An Extracellular Agarase from a *Cytophaga* Species, *Biochem. J.*, (1969), pp. 113, 139.

Kadokami, Yoichi and Lewis, Randolph V., Reverse Electrophoresis to Concentrate DNA Fractions, *Analytical Biochemistry*, (1995), 226: pp. 193–195.

Gnirke, Andreas; Huxley, Clare; Peterson, Ken and Olson, Maynard V., Microinjection of Intact 200– to 500–kb Fragments of YAC DNA into Mammalian Cells, (1993), *Genomics*, 15: pp. 659–667.

Potier, M.–C.; Kuo, W.L.; Dutriaux, A.; Gray, J. and Goedert, M.; Construction and Characterization of a Yeast Artificial Chromosome Library Containing 1.5 Equivalents of Human Chromosome 21, (1992), *Genomics*, 14: pp. 481–483.

Maule, John C.; Porteous, David J. and Brookes, Anthony J., An improved method for recovering intact pulsed field gel purified DNA, of at least 1.6 megabases, (1994), *Nucleic Acids Research*, 22:15: pp. 3245–3246.

Gold, Paul, Use of a Novel Agarose Gel–Digesting Enzyme for Easy and Rapid Purification of PCR–Amplified DNA for Sequencing, (1992), *BioTechniques 133*, 13:1.

Carlsson, J. and Malmqvist, M., Effects of Bacterial Agarase Gel in Cell Culture, (1977), *In Vitro*, 13:7: pp. 417–422.

Gray, Forest; Kenney, John S. and Dunne, John F., Secretion capture and report web: use of affinity derivatized agarose microdroplets for the selection of hybridoma cells, (1995), *Journal of Immunological Methods*, 182: pp. 155–163.

Serwer, Philip; Hayes, Shirley J.; Moreno, Elena T. and Park, Christopher Y., A Small (58–nm) Attached Sphere Perturbs the Sieving of 40–80–Jilobase DNA in 0.2–2.5% Agarose Gels: Analysis of Bacteriophage T7 Capsid–DNA Complexes by Use of Pulsed Field Electrophoresis, (1992), *Biochemistry*, 31: pp. 8397–8405.

Hodgson, D.A. and Chater, K.F., A Chromosomal Locus Controlling Extracellular Agarase Productio by *Steptomyces coelicolor* A3(2), and its inactivation by Chromosomal Integration of Plasmid SCP1, (1981), *Journal of General Microbiology*, 124: pp. 339–348.

Kendall, Kevin and Cullum, John, Cloning and expression of an extracellular–agarase gene from *Steptomyces coelicolor* A3(2) in *Streptomyces lividans* 66, (1984), *Gene*, 29: pp. 315–321.

Belas, Robert; Bartlett, Douglas and Silverman, Michael, Cloning and Gene Replacement Mutagenesis of a *Pseudomonas atlantica* Agarase Gene, (Jan. 1988), *Applied and Environmental Microbiology*, pp. 30–37.

Rochas, Cyrille; Potin, Philippe and Kloareg, Bernard, NMR spectroscopic investigation of agarose oligomers produced by an α–agarase, (1994), *Carbohydrate Research*, 253: pp. 69–77.

Hofsten, B.V. and Malmqvist, M., Degradation of Agar by a Gram–negative Bacterium, (1975), *Journal of General Microbiology*, 87: pp. 150–158.

Epicentre Technologies Publication, GELase™ Agarose Gel–Digesting Preparation Product Information, (Aug. 1993), 5 pages.

New England Biolabs Publication, β–Agarase I, 3 pages.

Miscellaneous Biochemicals Publication, p. 263.

Alphabetical List of Compounds, *Sigma*, p. 54.

CALBIOCHEM® Biochemicals for Research, 121814 Agarase, *Pseudomonas atlantica*, p. 8.

FMC Corporation Publication, β–Agarase, 1 page.

Promega Technical Bulletin, Promega Corporation, Madison, Wisconsin, (Jun. 1995), pp. 1–17.

Knoche, Kimberly; Selman, Susanne; Kobs, Gary; Brady, Melinda and Knuth, Mark, Modifying Enzymes, (Oct. 1995), *Promega Notes Magazine*, 54: pp. 14–19.

Selman, Susanne; Knoche, Kim and Knuth, Mark, Modifying Enzymes, (Aug. 1995), *Promega Notes Magazine*, 53: pp. 6–11.

Zuklic, Frank W. (1992) *Characterization of Bacterial Marine Isolate NR19 and the Partial Purification of its Secreted Agarase* (Masters Degree Thesis submitted to the University of South Florida).

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Gln  Phe  Thr  His  Ile  Ser  His  His  Ser  Phe  Ile
1                   5                        10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Asp  Trp  Asn  Ser  Trp  Tyr  Asn  Asp  Asn  Arg
1                   5                        10
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Val  Thr  Ala  Asn  Tyr  Gly  Trp  Gly  Asp  Trp  Cys  Trp  Asn  Pro  Tyr
1                   5                        10                       15
```

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: N-terminal ( v i ) ORIGINAL SOURCE:
        ( A ) ORGANISM: Flavobacterium heparinum ( i x ) FEATURE:
        ( A ) NAME/KEY: misc_feature
        ( B ) LOCATION: complement (9)
        ( D ) OTHER INFORMATION: /note= "N at position 9 is an
            inosine residue"

( x i ) SEQUENCE DESCRIPTION: SEQ ID NO:4:

```
TGGAAYWSNT GGTAYAAYGA YAA                                          23
```

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: N-terminal ( v i ) ORIGINAL SOURCE:
        ( A ) ORGANISM: Flavobacterium heparinum ( i x ) FEATURE:
        ( A ) NAME/KEY: misc_feature
        ( B ) LOCATION: complement (7)
        ( D ) OTHER INFORMATION: /note= "N at position 7 is an inosine residue"

( i x ) FEATURE:
        ( A ) NAME/KEY: misc_feature
        ( B ) LOCATION: complement (13)
        ( D ) OTHER INFORMATION: /note= "N at position 13 is an inosine residue"

( x i ) SEQUENCE DESCRIPTION: SEQ ID NO:5:

CCARTCNCCC CANCCRTART T                      21

( 2 ) INFORMATION FOR SEQ ID NO:6:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: N-terminal ( v i ) ORIGINAL SOURCE:
        ( A ) ORGANISM: Flavobacterium heparinum ( x i ) SEQUENCE DESCRIPTION: SEQ ID NO:6:

TGATTGGTGC TGGNNTAACG GCACAGNCGN TATNTGAGAC TGGGTGTCTA TTGGGNAGGT    60

CCAAAACACT                                                70

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: N-terminal ( v i ) ORIGINAL SOURCE:
        ( A ) ORGANISM: Flavobacterium heparinum ( i x ) FEATURE:
        ( A ) NAME/KEY: misc_feature
        ( B ) LOCATION: complement (9..10)
        ( D ) OTHER INFORMATION: /note= "N at positions 9 and 10 are inosine residues"

( x i ) SEQUENCE DESCRIPTION: SEQ ID NO:7:

TGCCGTTANN CCAGCACCAA TCA                      23

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: N-terminal ( v i ) ORIGINAL SOURCE:
        ( A ) ORGANISM: Flavobacterium heparinum ( i x ) FEATURE:
        ( A ) NAME/KEY: misc_feature
        ( B ) LOCATION: complement (7)
        ( D ) OTHER INFORMATION: /note= "N at position 7 is an inosine residue"

( x i ) SEQUENCE DESCRIPTION: SEQ ID NO:8:

GGACCTNCCC AATAGACACC CAGTCTCA        28

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: N-terminal ( v i ) ORIGINAL SOURCE:
        ( A ) ORGANISM: Flavobacterium heparinum ( x i ) SEQUENCE DESCRIPTION: SEQ ID NO:9:

CCGATTATTT GATGTTACAC ATCCAGA        27

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: N-terminal ( v i ) ORIGINAL SOURCE:
        ( A ) ORGANISM: Flavobacterium heparinum ( x i ) SEQUENCE DESCRIPTION: SEQ ID NO:10:

GCGGCTAGTA ATAATTCGAA TGGAA        25

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( v ) FRAGMENT TYPE: N-terminal (v i) ORIGINAL SOURCE:
    (A) ORGANISM: Flavobacterium heparinum (x i) SEQUENCE DESCRIPTION: SEQ ID NO:11:

CAAGTATTAC CTGGTCCGGC ATAAG                                              25

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: DNA (genomic)

(v) FRAGMENT TYPE: N-terminal (v i) ORIGINAL SOURCE:
        (A) ORGANISM: Flavobacterium heparinum (x i) SEQUENCE DESCRIPTION: SEQ ID NO:12:

TGGAGGATCA AATGGTACAA CATGTG                                             26

(2) INFORMATION FOR SEQ ID NO:13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: DNA (genomic)

(v) FRAGMENT TYPE: N-terminal (v i) ORIGINAL SOURCE:
        (A) ORGANISM: Flavobacterium heparinum (x i) SEQUENCE DESCRIPTION: SEQ ID NO:13:

AAATTATGGC CCAAGAATGG AGTAACATT                                          29

(2) INFORMATION FOR SEQ ID NO:14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: DNA (genomic)

(v) FRAGMENT TYPE: N-terminal (v i) ORIGINAL SOURCE:
        (A) ORGANISM: Flavobacterium heparinum (x i) SEQUENCE DESCRIPTION: SEQ ID NO:14:

GCTTTCTAGA TAAAATCCCA CCATTAATGG CATA                                    34

(2) INFORMATION FOR SEQ ID NO:15:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: DNA (genomic)

(v) FRAGMENT TYPE: N-terminal (vi) ORIGINAL SOURCE:
 (A) ORGANISM: Flavobacterium heparinum (xi) SEQUENCE DESCRIPTION: SEQ ID NO:15:

TTCGTCATGA AAAAAACTA TTTAATCTTT TTGCTATC                                                             38

(2) INFORMATION FOR SEQ ID NO:16:

(i) SEQUENCE CHARACTERISTICS:
  (A) LENGTH: 1251 base pairs
  (B) TYPE: nucleic acid
  (C) STRANDEDNESS: single
  (D) TOPOLOGY: linear (ii) MOLECULE TYPE: DNA (genomic)

(v) FRAGMENT TYPE: N-terminal (vi) ORIGINAL SOURCE:
  (A) ORGANISM: Flavobacterium heparinum (xi) SEQUENCE DESCRIPTION: SEQ ID NO:16:

AGTAATTGGC AATCAAAATG AAGATGCTAT TTCTAATATC TAAACTTAAA CCATAGCCTA      60

ATACGACTAG GCTTACTTAA CTTTTTCGAA ATGAAAAAAA ACTATTTAAT CTTTTGCTA      120

TCATTCTTTT GGGCATTATT AGTGAACGCC CAAGAATGGA GTAACATTCC TGTCCCTGCT     180

TATGCCGGAC CAGGTAATAC TTGGGAACTT CAGAGCAATC TTTCTGATGA TTTTAACTAC     240

AATTTCAACG CTGTAAACTA CAAAACAAAC TTTGGTAACG GAAAGTGGTA TAACTTTTAC     300

CATAATGGTT GGGATGGTCC CGGAACGACT TACTGGGTGC ATAACAAAGT GAAAGTTGAT     360

GGAGACAATC TAGTCATTAC TGTCTCAAAA AGTAATAACA CGTCTAAAAT GGGTATTCCT     420

GGAGTATTTT CTGGATGTGT AACATCAAAT AATCGGGTAG TTTATCCGGT TNATGTGGAG     480

TCGGCCATTA GTGTAGCCAA CATATCATTA GCTTCTTGTT TTTGGTTATT GAGTCCCGAT     540

GACACTCAAG AAATTATATC ATTGAGAACN NATGGTAATG TACCTTGGTT CAAACAATTT     600

ACCCACATCA GTCACCACTC TTTTATTCGT ACGCCATTTA CTGATTATCA ACCAAAGGAT     660

TGGAACAGTT GGTACAACGA TAACAGAGTA ACAGCCAATT ATGGCTGGGG TGATTGGTGC     720

TGGAATAACG GCAACAGAAG ATATATGAGA ATGGGTGTTT ATTGGGTAGG TCCAAAACAC     780

TTTGAATATT ATATCGATGG TCAACTCGTT CGAGTGATGT ACCATAATGC TACTGCGACA     840

AAAGTAAATG GAACATGGGA ATATCAGTAT TTCAATGCTA TGAATGGACA GTTTCCTGCC     900

AATAATGCTA ATGGCTATAC CGCTGTCACT ACCTATACTA CTAGTTCTAC TTATAGTTTC     960

CCTACTATTC AAGCGGCTAG TAATAATTCG AATGGAATTA GTGTTATTGA CCCGGGTAAT     1020

TTCCAAGGTG GAGCTGGATT TACAAAAGCC ATGGACATTA TTATTAATGT AGAGTNTCAA     1080

CAATGGTTGG CTTTAAACCA CACTCCTTCT GATGCTGATT TGGCAAGTTC AGCTAGAAAC     1140

CAAATGAAAG TCGATTGGGT GAGGGTTTAT AAACCTAAGA GTGCTTCGGG NTGGAGGATC     1200

AAATGGTACA ACATGTGCCG ATGCTCCTAC TTACAATGGC AACTCAAATA G              1251

(2) INFORMATION FOR SEQ ID NO:17:

(i) SEQUENCE CHARACTERISTICS:
  (A) LENGTH: 367 amino acids
  (B) TYPE: amino acid
  (C) STRANDEDNESS:
  (D) TOPOLOGY: linear (ii) MOLECULE TYPE: protein (xi) SEQUENCE DESCRIPTION: SEQ ID NO:17:

-continued

| | | | | | | | | | | | | | | |
|---|---|---|---|---|---|---|---|---|---|---|---|---|---|---|
| Ala 1 | Gln | Glu | Trp | Ser 5 | Asn | Ile | Pro | Val | Pro 10 | Ala | Tyr | Ala | Gly | Pro 15 | Gly |
| Asn | Thr | Trp | Glu 20 | Leu | Gln | Ser | Asn | Leu 25 | Ser | Asp | Asp | Phe | Asn 30 | Tyr | Asn |
| Phe | Asn | Ala 35 | Val | Asn | Tyr | Lys | Thr 40 | Asn | Phe | Gly | Asn | Gly 45 | Lys | Trp | Tyr |
| Asn | Phe 50 | Tyr | His | Asn | Gly | Trp 55 | Asp | Gly | Pro | Gly | Thr 60 | Thr | Tyr | Trp | Val |
| His 65 | Asn | Lys | Val | Lys | Val 70 | Asp | Gly | Asp | Asn | Leu 75 | Val | Ile | Thr | Val | Ser 80 |
| Lys | Ser | Asn | Asn | Thr 85 | Ser | Lys | Met | Gly | Ile 90 | Pro | Gly | Val | Phe | Ser 95 | Gly |
| Cys | Val | Thr | Ser 100 | Asn | Asn | Arg | Val | Val 105 | Tyr | Pro | Val | Xaa | Val 110 | Glu | Ser |
| Ala | Ile | Ser 115 | Val | Ala | Asn | Ile | Ser 120 | Leu | Ala | Ser | Cys | Phe 125 | Trp | Leu | Leu |
| Ser | Pro 130 | Asp | Asp | Thr | Gln | Glu 135 | Ile | Ile | Ser | Leu | Arg 140 | Xaa | Xaa | Gly | Asn |
| Val 145 | Pro | Trp | Phe | Lys | Gln 150 | Phe | Thr | His | Ile | Ser 155 | His | His | Ser | Phe | Ile 160 |
| Arg | Thr | Pro | Phe | Thr 165 | Asp | Tyr | Gln | Pro | Lys 170 | Asp | Trp | Asn | Ser | Trp 175 | Tyr |
| Asn | Asp | Asn | Arg 180 | Val | Thr | Ala | Asn | Tyr 185 | Gly | Trp | Gly | Asp | Trp 190 | Cys | Trp |
| Asn | Asn | Gly 195 | Asn | Arg | Arg | Tyr | Met 200 | Arg | Met | Gly | Val | Tyr 205 | Trp | Val | Gly |
| Pro | Lys 210 | His | Phe | Glu | Tyr | Tyr 215 | Ile | Asp | Gly | Gln | Leu 220 | Val | Arg | Val | Met |
| Tyr 225 | His | Asn | Ala | Thr | Ala 230 | Thr | Lys | Val | Asn | Gly 235 | Thr | Trp | Glu | Tyr | Gln 240 |
| Tyr | Phe | Asn | Ala | Met 245 | Asn | Gly | Gln | Phe | Pro 250 | Ala | Asn | Asn | Ala | Asn 255 | Gly |
| Tyr | Thr | Ala | Val 260 | Thr | Thr | Tyr | Thr | Thr 265 | Ser | Ser | Thr | Tyr | Ser 270 | Phe | Pro |
| Thr | Ile | Gln 275 | Ala | Ala | Ser | Asn | Asn 280 | Ser | Asn | Gly | Ile | Ser 285 | Val | Ile | Asp |
| Pro | Gly 290 | Asn | Phe | Gln | Gly | Gly 295 | Ala | Gly | Phe | Thr | Lys 300 | Ala | Met | Asp | Ile |
| Ile 305 | Ile | Asn | Val | Glu | Xaa 310 | Gln | Gln | Trp | Leu | Ala 315 | Leu | Asn | His | Thr | Pro 320 |
| Ser | Asp | Ala | Asp | Leu 325 | Ala | Ser | Ser | Ala | Arg 330 | Asn | Gln | Met | Lys | Val 335 | Asp |
| Trp | Val | Arg | Val 340 | Tyr | Lys | Pro | Lys | Ser 345 | Ala | Ser | Xaa | Trp | Arg 350 | Ile | Lys |
| Trp | Tyr | Asn 355 | Met | Cys | Arg | Cys | Ser 360 | Tyr | Leu | Gln | Trp | Gln 365 | Leu | Lys | |

ISOLATED AGARASE ENZYME FROM FLAVOBACTERIUM SP. STRAIN NR19, CLONED GENES THEREFOR, AND EXPRESSION THEREOF IN TRANSFORMED HOST CELLS

FIELD OF THE INVENTION

The present invention relates to novel agarases for the digestion of agarose into oligosaccharide chains, deoxyribonucleic acid (DNA) molecules which encode the novel agarase, cloned DNA molecules which encode the novel agarase, plasmids and vectors containing the cloned DNA molecules, and transformed organisms which express the novel agarase with its agarase activity intact.

CITED REFERENCES

Full bibliographic citations of the references cited hereinbelow can be found in the Bibliography section, immediately preceding the Sequence Listing.

DESCRIPTION OF THE PRIOR ART

Agarose, or more correctly, agaroses, are widely used as gels in the electrophoretic separation of deoxyribonucleic acid (DNA) and ribonucleic acid (RNA). Agarose is capable of forming gels which allow DNA or RNA strands to be separated without destroying the activity of the DNA or RNA molecules. A highly heterogeneous polysaccharide, agarose is an alternating co-polymer of 3-linked β-D-galactopyranose and 4-linked 3,6-anhydro-α-L-galactopyranose.

To form an agarose gel for electrophoretic purposes, a hot solution of agarose is prepared. The hot agarose solution is then cast in an electrophoresis apparatus and allowed to cool. As the solution cools, it reaches a loose gel state, i.e., the gelling point where agarose chains form double helices which join together to form loosely associated bundles or fibrils (the Gel I state). As the gel cools further still, the bundles further associate with each other to form a point where the bundles of agarose chains associate with each other to form a hardened agarose gel structure is formed (the Gel II state). It is this Gel II structure which is widely used in agarose gel electrophoresis (Kin, N. M. et al., 1972).

High purity agarose for gel electrophoretic purposes is essentially a commodity item, and is commercially available from a number of national suppliers. For instance, LMP Preparative Grade Agaroses are available from the Promega Corporation, Madison, Wis. Similar agaroses can also be obtained from the FMC BioProducts Corporation, Rockland, Me.

The conventional procedure for agarose gel electrophoresis begins by the casting of an agarose gel (Gel II) in a suitable electrophoresis chamber. Tris/acetate buffer (TAE) or tris/borate buffer (TBE) is typically included in the molten gel solution. The DNA or RNA then is loaded into the gel and electrophoresed. After the electrophoresis is complete, and the band visualized by suitable means, a second procedure is begun to harvest the nucleic acids of interest from the agarose gel.

As is well known in the art, to harvest nucleic acids from an agarose gel, the gel fraction of interest is physically excised from the remainder of the gel. A number of methods can then be employed to harvest the DNA/RNA from the gel. One commonly used method employs an agarase enzyme, which hydrolyzes the gel, liberating the DNA/RNA. The conventional harvesting protocol using agarase enzymes proceeds as follows: First, the electrophoresis buffer is exchanged for an agarase reaction buffer more favorable for agarase activity. This buffer exchange is necessary because the conventional agarase enzymes, described infra., which are used in subsequent gel manipulations, generally are less active in pH/salt conditions usually used for electrophoresis.

The solid agarose gel is then melted by heating to temperatures of approximately 65° to 100° C., depending on the type of agarase. Currently, it is necessary to melt the gel because commercially available agarases will not digest unmelted agarose. This is thought to be due to the tight, interlocking nature of the agarose Gel II state, which sterically prohibits access of the agarase enzymes to the interior of the agarose chains. Unfortunately, temperatures above 75° C. may result in thermal degradation of the desired nucleic acid contained within the agarose. For this reason, only low melting point temperatures (65°–75° C.) can be used with this procedure.

Once the agarose has been completely melted, the gel is equilibrated at a lower temperature of about 42° to 45° C., the temperature at which the now commercially available agarase enzymes exhibit optimum agarose digesting activity. Once the gel has equilibrated at the proper temperature, agarase is added to the gel and allowed to digest the agarose into small neoagarooligosaccharide chains. The nucleic acids contained in the gel can then be separated from the small oligosaccharide fragments of the now-digested gel by a variety of means, including ethanol precipitation.

A major drawback of this procedure is that two competing physical phenomena are at play. On the one hand, the gel must be melted at suitably high temperatures in order for the matrix to be completely disassociated so that the agarose chains are accessible to the agarase enzyme. However, at these high temperatures, agarase enzymes subsequently added to the gel are often adversely affected. For instance, if the agarase is added to the agarose too quickly after melting, the agarase can be completely inactivated.

On the other hand, if the agarose gel is allowed to equilibrate at a lower temperature for too long, the Gel I state can reform. Because the agarase enzyme cannot digest the re-formed gel, only partial digestion of the agarose gel is achieved. This results in incomplete recovery of the nucleic acids of interest. As a result, there is a strong motivation to carry out the enzyme digestion at a reasonably high temperature so as to inhibit gel re-formation while simultaneously avoiding thermal inactivation of the nucleic acid sample and the agarase enzyme itself.

Clearly then, there is a distinct need for an agarase enzyme which exhibits better high-temperature stability, thereby allowing digestion to proceed at a higher temperature, where Gel I state formation is not as problematic. There is also a need for a new form of agarase which is active in a wide variety of electrophoresis buffers and under wide pH and solute conditions, thereby obviating the need to exchange the electrophoresis buffer for a different reaction buffer.

Regarding known agarases themselves, commercially available agarase isolated from *Pseudomonas atlantica* can be purchased from a large number of national suppliers, such as the New England Biolabs Corporation (Beverly, Mass.). Additionally, a commercially-available agarase isolated from an unknown organism can be purchased from Epicentre Technologies (Madison, Wis.).

FIG. 1 is an electrophoretogram comparing several commercially-available prior art agarases and an agarase of the present invention. Here, approximately 2 μg of each enzyme was heated in the presence of sodium dodecylsulfate polyacrylamide gel electrophoresis (SDS-PAGE) sample buffer, electrophoresed on a pre-cast 4–20% polyacrylamide gradient gel and stained with COOMASSIE blue.

Lane M of FIG. 1 shows Promega Corporation's (Madison, Wis.) Mid-Range Protein Molecular Weight Markers. Lanes 1–6 of FIG. 1 depict agarases purchased from six different commercial vendors. Lanes 2–5 are agarase enzymes isolated from *Pseudomonas atlantica*. This agarase has a molecular weight of 32 kilodalton (kD). The enzyme preparation in Lane 3 contains bovine serum albumin added by the vendor, hence the additional band. Lanes 1 and 6 depict the other commercially available agarase enzyme purified from an unknown species. This agarase has a molecular weight of approximately 45 kD. Lane P contains an agarase of the present invention, and will be discussed in full, below.

Several other agarase enzymes, isolated from a variety of microorganisms, are described in the scientific literature. For instance, Sugano et al. (1993b) and Sugano et al. (1994) describe the isolation and characterization of two different agarase enzymes from Vibrio sp. strain JT0107. Sugano et al. (1993b) describe an agarase gene from the JT0107 strain which was designated agaA. The agarase encoded by this gene was shown to have a molecular weight of approximately 105 kD. The authors initially designated the mature protein "agarase 0107." In Sugano et al. (1994), a distinct agarase gene (designated agaB) was cloned from the genomic DNA of the same Vibrio sp. strain JT0107. A portion of the cloned gene was expressed in *E. coli.* to yield a protein with agarase activity. The authors note that this was the first evidence that more than one type of agarase is produced by the JT0107 strain.

An earlier work by Sugano et al. (1993a) describes a marine bacterial strain that decomposes the cell walls of some types of seaweed. This strain was also classified to the genus Vibrio. Sugano et al. identified a novel β-agarase from this organism which was found to migrate as a single band of molecular weight 107 kD on SDS-PAGE. This particular agarase was found to have an optimum temperature of 30° C.

An α-agarase isolated from *Alteromonas agarlyticus* strain GJ1B having a molecular weight of 180 kD is described by Potin et al. (1993). Here, the agarase was shown to specifically cleave agarose at the 1–3 alpha linkages to yield predominantly agarotetraose. Further study of the isolated enzyme suggested that the native enzyme is a dimer of 360 kD molecular weight which is dissociated into active sub-units by the anion exchange protocol used to isolate the enzyme. This particular enzyme was shown to be inactivated by pH's below 6.5, or by temperatures above 45° C.

Several other distinct agarase enzymes, isolated from various Vibrio and Pseudomonas strains, as well as strains of *Streptomyces coelicolor*, are described in the scientific literature. See, for instance, Aoki et al. (1990); Belas (1989); Bibb et al. (1987); and Morrice et al. (1983).

In the patent literature, a heterogeneous agarase enzyme system from *Spartina alterniflora* strain 2–40 (ATCC No. 43961) is described in U.S. Pat. No. 5,418,156, to Strosz et al. Of particular note in Strosz et al. is that the inventors are uncertain whether it is only a single enzyme or a collection of enzymes which is responsible for the agarolytic activity displayed by the 2–40 strain and the *E. coli.* transformants. The patent describes concentrating a cell supernatant by passing the supernatant through a molecular sieve with 30 kD nominal molecular weight cut-off limit. The agarase activity was found to be retained within the retentate having a molecular weight above 30 kD. The retentate was then fractionated on a non-denaturing polyacrylamide protein separation gel and the band(s) tested for agarolytic activity. However, the reference does not describe which band(s) in the resultant gel display agarase activity, nor does this reference assign a molecular weight to any of the active band(s). Equally ambiguous results are described for a separation procedure using gel permeation chromatography.

Regarding Flavobacterium sp. strain NR19, this bacterium and its agarolytic activity was first described by Zuklic (1992). The bacterium was isolated from the mucus layer of a coral found in the Dry Tortugas. NR19 is Gram-negative and rod-shaped. NR19 has been classified to the genus Flavobacterium based upon its cultural, morphological, and biochemical characteristics. The thesis describes several tests which failed to match the NR19 strain with any known organism. Additionally, the thesis describes the properties of the NR19 strain which distinguish it from organisms of the Pseudomonas, Vibrio, Cytophaga, and Alteromonas genera (all of which are known to produce agarases).

The stated goal of the thesis was to isolate the enzyme or enzymes responsible for the agarolytic activity of this bacterium. However, the author was successful only in achieving partial purification of a fraction containing agarase activity from "at least one minor distinct agarase." This work does not identify or isolate a single agarase activity of defined molecular weight produced by the NR19 strain.

None of the above-described references, taken alone or in any combination, is seen as describing the invention disclosed hereinbelow.

SUMMARY OF THE INVENTION

In light of the above discussion, it is a principal aim of the present invention to provide a novel purified agarase enzyme which is useful for a number of purposes, including the digestion of agarose electrophoresis gels.

It is a further aim of the present invention to provide a purified agarase enzyme isolated from Flavobacterium sp. strain NR19 ATCC 202009 which exhibits a high level of agarase activity.

The present invention is directed to an isolated and purified agarase from Flavobacterium sp. strain NR19.

The present invention is further directed to an isolated gene encoding an agarase enzyme having a molecular weight of 42 kD by SDS-PAGE, the gene being isolated from Flavobacterium sp. strain NR19.

A further aspect of the present invention is an isolated gene encoding an agarase enzyme having a molecular weight of 42 kD by SDS-PAGE, wherein the agarase enzyme encoded by the gene has an amino acid sequence as shown in SEQ. ID. NO: 17.

Also, recombinant DNA constructs comprising a gene isolated from Flavobacterium sp. strain NR19, which encodes an agarase enzyme are included in the present invention.

Further still, recombinant plasmid vectors for the expression of an agarase enzyme, the plasmid vectors comprising a DNA insert isolated from Flavobacterium sp. strain NR19 are part of the present invention.

Another aspect of the present invention is a transformed host cell comprising a heterologous gene isolated from Flavobacterium sp. strain NR19 which encodes an agarase enzyme.

The present invention also is directed to an antibody specifically reactive against a 42 kD agarase enzyme from Flavobacterium sp. strain NR19.

The novel agarase enzyme of the present invention provide for the digestion of agarose electrophoresis gels which have fast hydrolysis rates, exhibit good thermal stability, and remain active at high pHs so as to eliminate the need to exchange buffers prior to initiating the digestion reaction.

These and other aims, objects, and advantages of the present invention will become clear upon a complete reading of the Detailed Description, claims, and drawing figures, below.

DETAILED DESCRIPTION OF THE INVENTION

Overview

Figure 1:
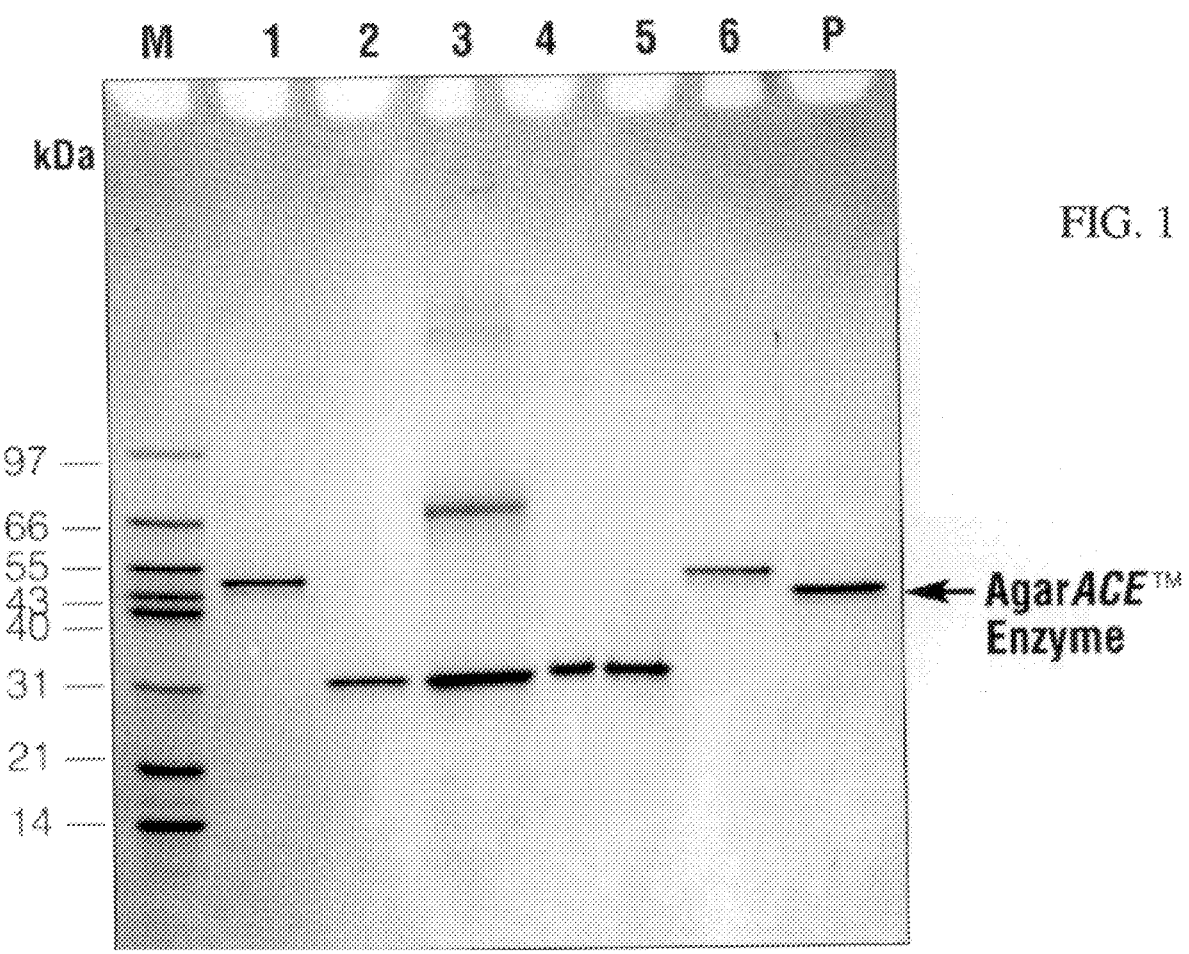
FIG. 1 is an electrophoretogram of several commercially-available prior art agarases and the 42 kD agarase of the present invention.

Isolation and characterization of the novel agarase of the present invention and the gene therefor proceeds in a stepwise fashion which begins with the isolation of two distinct extracellular agarase enzymes from Flavobacterium sp. strain NR19 ATCC 202009. One agarase of the present invention has a molecular weight of approximately 42 kD as measured by SDS-PAGE, while a second, distinct agarase has a molecular weight of approximately 105 kD.

After isolation of the two enzymes, the amino acid sequences of the enzymes are partially determined. Armed with knowledge of the amino acid sequences, corresponding synthetic oligonucleotide probes are constructed and used to probe a complete genomic library of NRl9 for complementary sequences.

Positive clones are then isolated, purified, and the DNA constructs sub-cloned into expression plasmids. The DNA sequences within the plasmids are then sequenced and verified. After sequence verification, the plasmids are used to direct expression of the functional agarase enzymes in a heterologous host, preferably E. coli.

The isolated and purified enzymes can then be used in the production of polyclonal and monoclonal antibodies which are specifically reactive against the individual agarases described herein.

Each of the above steps, and various methods to accomplish each of the steps, are described in full, below:

Culturing Flavobacterium sp. Strain NR19

Because Flavobacterium sp. strain NR19 is a marine organism, it is conventionally cultured in an artificial seawater medium. Such artificial seawater media are well known to those skilled in the art. An illustrative, and preferred, artificial seawater preparation is prepared as follows (for one liter of medium):

2 grams (g) yeast extract (Difco Labs, Detroit, Mich.)
10 g bacto peptone (Difco Labs)
22.07 g NaCl
Add 500 milliliters (ml) deionized water Mix thoroughly until the above components are completely dissolved, and add the following:

20 ml of 2M $MgSO_4(7H_2O)$
10 ml of 0.75M KCl
10 ml of 0.2M $NaHCO_3$
10 ml of 70 mM KBr
10 ml of 13 mM $SrCl(6H_2O)$
50 ml of 2M Tris buffer (pH 7.3)
10 ml of Macro Nutrients solution*
10 ml of Trace Element solution**

* Macro Nutrients solution:
    0.24 g $Na_2HPO_4$
    0.072 g NaF
    0.048 g $NH_4NO_3$
    0.12 g Na-meta silicate
    add deionized water to 300 ml

** Trace Mineral solution:
    3 g $Na_2EDTA$
    0.384 g $FeCl_3(6H_2O)$
    0.432 g $MnCl_2(4H_2O)$
    0.342 g $H_3BO_3$
    0.04 g $ZnSO_4(7H_2O)$
    2 mg $CoCl_2(6H_2O)$
    0.25 mg $CuCl_2$
    add deionized water to 1200 ml Add 2 g agarose and heat the solution slightly to get the agarose into solution. Then add deionized water to bring the total solution volume to 990 ml, and add 10 ml of 1.6M $CaCl_2(2H_2O)$ to yield 1 liter of modified artificial seawater medium. The medium is then autoclaved to sterilize. Autoclave time is important: no more than 20 minutes at sterilization temperatures, or agarose will degrade and fail to stimulate agarase production.

An inoculum of NR19 readily thrives upon the above-described artificial seawater medium. For optimum growth, NR19 is preferably cultured in a 500 ml volume of artificial seawater medium in a 2 L flask at a temperature of 30° C. under constant agitation.

To culture NR19 for the optimum production of agarase enzymes, the following protocol is preferred:

A 0.5 ml frozen seed sample of NR19 cells is aseptically transferred into a flask containing 500 ml of the above-described artificial seawater medium. The flask is then placed in an orbital shaker set at shaking speed of 200 rpm, and incubated at a temperature of 30° C. for approximately 20 hours. At this point, the medium should be quite turbid and orange in color, and have an odor not unlike that of a wet dog.

To test the culture for agarase production, a 10 ml sample is aseptically taken from the culture. To confirm that the cultures have reached at least 20 U agarase activity/ml, the agarase activity assay described below is run, and absorbance of the resulting samples is measured at 450 nm. See below for a complete description of the method used to assay agarase activity. If the culture has not reached 20 U/ml within approximately 20 hours, it can be further incubated and monitored until this level of production is reached.

To begin harvesting the agarase enzymes from the culture, the culture is centrifuged at 21,000 X g for 0.5 hour. Agarase activity is retained in the supernatant. The supernatant can be stored at 4° C. with the addition of 0.02% $NaN_3$ for up to a week until further processing. It has also been found that the supernatant can be stored for at least 6 months at −20° C. without adverse effects on the resulting agarase products.

Assay for Agarase Activity

Throughout the agarase isolation manipulations, it is necessary to test the various fractions for agarase activity to monitor the efficiency of the various separation steps. The following protocol is the preferred method used herein for assaying agarase activity (Dygert, S. et al., 1965):

First, the following solutions are prepared in advance:

1. D-galactose standard: Prepare a 1 mg/mL stock solution of D-galactose (Sigma Chemical, St. Louis, Mo.) in water.

2. Assay Solution A—Neocuproine: Place 610 mg of neocuproine hydrochloride (Sigma Chemical) in a beaker on stirplate with a stir bar. Add 500 ml of deionized water and stir until the solids are completely dissolved. This solution should be stored at room temperature and protected from light in an opaque plastic bottle. The final concentration of neocuproine is 5 mM. This solution will remain functional for approximately 6 months.

3. Assay Solution B—Sodium Carbonate, Glycine, Cupric Sulfate: Place 490 ml of deionized water in a beaker on stirplate with a stir bar. Add 20 g anhydrous sodium carbonate (Fisher Scientific, Pittsburgh, Pa.), and stir until solids are completely dissolved. Next, add 8 g glycine and 0.23 g cupric sulfate pentahydrate ($CuSO_4 \times 5\ H_2O$) (both available from Sigma), stir until solids are completely dissolved, and adjust to 500 ml with deionized water. Store at room temperature in a glass bottle. Final concentrations are 377 mM sodium carbonate, 213 mM glycine, 1.85 mM cupric sulfate. This solution also remains good for at least 6 months.

4. Assay Solution C—Prepared from Assay Solutions A and B: Prepare this solution just prior to starting the assay. Mix equal parts Assay Solutions A and B. Store at room temperature. This solution is preferably used within 2 hours, and should be protected from light if stored more than 30 minutes.

5. Assay Solution D—0.15 % SEAPLAQUE GTG Agarose (FMC BioProducts, Rockland, Me.) in 1x TAE pH 7.2: Add 10 ml of 10x TAE, pH 7.2, to 90 ml of deionized water in a screw cap bottle. Add 150 mg of SEAPLAQUE GTG agarose, loosely cap bottle and tare on a top-loading balance. Gently heat bottle with occasional swirling until agarose is completely melted. Place bottle back on the balance, and add water until the original weight is reached. The added water replaces the water that has evaporated, which ensures that the net agarose concentration in the solution is accurate. Store tightly capped at 37° C. until use, or tightly capped at room temperature. If stored at room temperature, re-melt before using. This solution is good for approximately 1 month, or 6–8 re-melting steps.

First, develop a galactose standard curve. This is done by placing, 0, 10, 20, 40, 60, and 80 $\mu l$ of the 1 mg/ml D-galactose standard into 25 ml screw-cap tubes. Add deionized water to bring each to 500 $\mu l$ total volume. Add 4 ml Assay Solution C to each tube, then cap, boil 10 minutes, and add water to 10 ml after cooling. Read samples at 450 nm, and plot OD 450 nm versus $\mu g$ galactose. From the slope and intercept of the line, it can be determined how many $\mu g$'s galactose produce 1 OD 450 for any given spectrophotometer. If the result is not 58 ug, the actual result can be substituted into the derivation and specific activity equations also described below.

Next, assay test samples. Prepare Assay Solution C just before the experiment by mixing equal parts Assay Solutions A and B. 4 ml of Solution C is required for each color reaction at each time point reading. Fill the required number of 25 ml screw cap tubes with 4 ml each of Assay Solution C.

In a water bath at 38°–42° C., place a corresponding number of disposable glass tubes, add 2 ml of Assay Solution D, and allow 2–3 minutes to equilibrate to the bath temperature. To start the assay reaction, add 1–50 $\mu L$ test material to the tubes containing Assay Solution D and mix by vortexing briefly. Immediately remove 500 $\mu l$ of the reaction cocktail and add it to a screw cap tube containing Assay Solution C and mix briefly. This constitutes the zero timepoint. In the identical fashion, take two more timepoints at 2 and 4 minutes.

When all the samples have been taken, cap the tubes tightly, and place them in a boiling water bath for 10 minutes. Try to place all the tubes into the boiling water within 15 seconds. Remove the tubes, allow them to cool, then add water to 10 ml.

Mix well by vortexing, and then read absorbance at 450 in a spectrophotometer. If absorbance at 450 nm is greater than 1.2, there was not enough color reagent to accurately detect all the galactose released, and assay must be repeated. Subtract the 450 nm absorbance of the zero timepoint from the 450 nm absorbencies obtained for the other timed samples. Calculate the activity as follows, using the zero-corrected absorbencies for each timepoint. The average of the value obtained for the two timepoints is used as the assay result.

The unit concentration and specific activity equations are derived as follows:

180 $\mu g$=1 $\mu mol$ D-galactose—The standard unit definition.

Enzyme units (pU's) are expressed as $\mu mol$ D-galactose/min.

Specific activity=$\mu mol$ D-galactose/min/mg protein

1 Enzyme Unit=$(1\ \Delta A_{450}/\text{minute})(1/\epsilon)$.

$1/\epsilon$=(58 $\mu g$ D-galactose/1 $A_{450}$), (180 $\mu g$ D-galactose/$\mu mol$=10 ml)=0.032***

1 Enzyme Unit=$(1\ \Delta A_{450}/\text{minute})(0.032)$

Unit Concentration =

$(1\ \Delta A_{450}\ \text{observed/time of } rxn \text{ in minutes})(0.032)(1000/\mu l\ \text{sample}) = U/\text{ml}$ Specific Activity =

Unit Concentration (U/ml) ÷ Protein Concentration (mg/ml) = U/mg

***(Empirical value. For different experimental conditions, re-calculate the value of 1/$\epsilon$ to derive a new constant).

Isolation of Distinct Agarase Enzymes

Two distinct and novel agarases, a first agarase having a molecular weight of approximately 42 kD and a second agarase having a molecular weight of approximately 105 kD, can be isolated in pure form from the supernatant of the above described culture.

The preferred isolation and purification procedure is accomplished in three distinct manipulations. First, the crude supernatant is passed over a ceramic hydroxyapatite resin or a resin of equivalent functionality. This first step serves to remove the majority of odiferous pigments and other contaminating proteins from the supernatant.

In a second step, the permeate is desalted and concentrated. This can be accomplished by any number of conventional means, such as ultrafiltration. The purpose of this step is to concentrate the sample to a volume suitable for efficient processing through the next column, and to remove the high levels of salt present in the original culture supernatant so that the remaining impurities will be bound to the ion exchange resin of the final step.

In a final purification step, the desalted and concentrated extract is passed over an anion exchange resin to separate the 42 kD agarase which flows through the resin from the 105 kD agarase, which binds to the resin and can be eluted with phosphate ions.

It is significant to note that agarases tend to attack and destroy or irreversibly bind to a number of common column resins. In general, most agarose or agarose-derived resins will present insurmountable barriers to achieving a clean separation. Also, very tight binding has been observed to a number of resins with polycarbohydrate moieties. Attempts to exploit this binding for separation purposes proved to be problematical due to its variability from run to run.

To illustrate the above steps and to further aid in a complete understanding of the present invention, the following protein isolation example is provided. This example is illustrative only and does not limit the invention described or claimed herein in any fashion. Commercial suppliers are noted for the resins used in the following example. Identical resins and resins having equivalent functionality are available from many different national suppliers.

Example of NR19 Culture and Agarase Isolation

The following Example is included solely to aid the reader in a full and complete understanding of the present invention. The Example does not limit the scope of the invention disclosed and claimed herein in any fashion.

Several cultures of Flavobacterium sp. strain NR19 were prepared in accordance with the above-described protocol. After 20 hours, the cultures were centrifuged to pellet the cellular debris and the pooled supernatants were used as the starting material in the following manipulations. All processing steps were done at room temperature unless otherwise indicated. This example started with approximately 20 liters of supernatant.

Ceramic Hydroxyapatite Flowthrough

The purpose of this step is to remove a significant amount of the odiferous pigment present in the initial supernatant, which would otherwise foul the concentration membranes and resins in the subsequent steps. The pigments bind to the hydroxyapatite resin. This step also removes a large majority of contaminating proteins, which also bind to the resin.

The major proteins that will be found in the flowthrough fraction are the 42 kD agarase and the 105 kD agarase. The supernatant from the shake flask culture is loaded directly onto the column head. This pass is best performed at room temperature. This particular resin cannot be exposed to acidic conditions because it will dissolve.

A 9 cm diameter Amicon column (Beverly, Mass.) was packed with 2 liters of BioRad MACROPREP (Hercules, Calif.) ceramic hydroxyapatite resin. The column was washed with 2 column volumes of 400 mM potassium phosphate, pH 6.8, at a flowrate of 200 ml/min. The column then was equilibrated with 6 column volumes of 1 mM potassium phosphate, pH 6.8, at 100 ml/min. Conductivity was checked to ensure that the column is properly equilibrated.

The column was then loaded with the supernatant, and the flowrate adjusted to 80–100 ml/min. Six 0.5 liter fractions were collected, and then 1 liter fractions until the supernatant was completely loaded. Next, the column was washed with 4 liters of 1 mM potassium phosphate, pH 6.8, and 1 liter fractions collected. 1/100 volumes of 2% sodium azide were added to each fraction to prevent any bacterial growth during storage. The agarases were found in the flowthrough fractions of this column.

The fractions were analyzed by SDS-PAGE, including molecular weight (MW) markers and reference samples of agarase as control lanes. In early fractions, only the 42 kD agarase eluted as the major band. A little later in the load, the 105 kD agarase eluted as a second major band. Toward the end of the load, a number of other protein contaminants eluted. The fractions containing the 42 kD and 105 kD agarases were then pooled.

Concentration and Desalting by Ultrafiltration

The pooled fractions from the proceeding step were then concentrated and desalted by passage through a molecular filter with a nominal 10,000 molecular weight cut-off.

A 5 ft$^2$ PELLICON (Millipore Corporation, Marlborough, Mass.) 10,000 NMWL (nominal molecular weight limit) membrane was cleaned as per manufacturer's instructions, and then flushed with 2 L of 1 mM potassium phosphate, pH 6.8. The hydroxyapatite flowthrough fractions were concentrated at 20 psi inlet pressure, 10 psi outlet pressure, about 100 ml/min crossflow rate, until the holdup volume was reached (about 650 ml). The permeate was discarded. 2.5 L of 1 mM potassium phosphate, pH 6.8, was added, and ultrafiltered to the holdup volume, and repeated until constant conductivity was achieved. This generally requires at least two additional passes. The permeate was discarded after checking conductivities.

The retentate then was harvested from the filter by back-flushing. (It is best to avoid foaming by keeping the flowrate below 20 ml/min). An additional 2×100 ml of 1 mM potassium phosphate, pH 6.8, was circulated through the cassette, collected, and pooled with the original retentate. To prevent any bacterial growth during storage, 1/100 volume of 2 % sodium azide was then added to the retentate.

Anion Exchange

The purpose of this step is to remove any remaining pigment and to separate the 42 kD and 105 kD agarases. This step also removes contaminants with molecular weight greater than 200 kD, other minor protein contaminants evident by SDS-PAGE, and any residual DNA and/or RNA that may still be present in the preparation at this stage. Here again, the desired 42 kD agarase flows through the column, while the 105 kD agarase and the impurities bind to the column. To obtain the purified 105 kD agarase, a salt gradient is used to elute the column.

In this example, the buffer in the input sample (1 mM phosphate, pH 6.8) did not match the buffer (20 mM TrisCl, pH 7.3) to which the column is equilibrated. However, in multiple tests, reproducible results were obtained in spite of this difference.

A 100 ml column was packed with MACROPREP Q® (BioRad Laboratories) anion exchange resin, washed with 200 ml 2M TrisCl, pH 7.3, at a flowrate of 4 ml/min, and then equilibrated to 20 mM TrisCl, pH 7.3. The ultrafiltered retentate from the above step was loaded onto the column at a flowrate of 4 ml/min. After the sample was completely loaded, the column was washed with 400 ml of 20 mM TrisCl, pH 7.3.

Four 100 ml fractions, one 500 ml fraction, and then several 100 ml fractions of the load were collected. 1/100 volume of 2% sodium azide was added to each fraction. The fractions were analyzed by SDS-PAGE, and the fractions displaying only a single band were pooled.

No detectable level of the 105 kD band remained in the pooled fractions. The pooled fractions were then stored frozen at $-20°$ C.

To obtain the 105 kD agarase, the column then was eluted with a 2 L gradient from 20 mM Tris, pH 7.3, to the same buffer containing 0.5M NaCl. 50 ml fractions were collected. The fractions were analyzed by SDS-PAGE, and pooled for purity of the 105 kD band. Agarase activity was assayed as described above. The pooled fractions were dialyzed into 20 mM Tris HCl, pH 7.3, and stored frozen at $-20°$ C.

Characterization of 42 kD Agarase Enzyme

When purified using the procedure above, the 42 kD enzyme runs as a series of 3–5 spots on 2 D gels, with an apparent pI of between 6.25 and 6.75. Referring now to FIG. 1, this figure depicts an SDS-PAGE electrophoretogram of several commercially-available agarase enzymes and the 42 kD agarase of the present invention. Lane M of FIG. 1 contains standard protein molecular weight markers. Lanes 1 and 6 depict agarases isolated from an unknown species having a molecular weight of approximately 45 kD. This agarase can be purchased from Epicentre Technologies (Madison, Wis.). Lanes 2 through 5 of FIG. 1 depict commercially-available agarases having a molecular weight of 32 kD. This agarase is isolated from *P. atlantica*. It can be purchased from several national suppliers. Lane P of FIG. 1 depicts the purified 42 kD agarase described above. As is evident from the electrophoretogram, this agarase does not show any contamination in the SDS-PAGE analysis. This analysis confirms that the agarase enzyme was, in fact, cleanly isolated by the above-described process.

Once the agarase was isolated, its ability to hydrolyze agarose was investigated. The extent of hydrolysis of agarose is determined by assaying for β-D-galactopyranose. When agarose is hydrolyzed, this sugar is released in a form that can reduce a chromogenic substrate. See Dygert, S. et al. (1965), which is incorporated herein by reference in its entirety. In the "transient release" (TR) method described above, a 0.15 percent solution of the same agarose in TBE buffer is treated for a short time (from 2–6 minutes) with agarase at a fixed temperature (usually 37° C.). The reaction is then stopped and assayed for sugar release. Since the agarose hydrolysis is generally incomplete at this shorter time period, this assay gives an estimate of the sugar release rate.

A second method, the "gel unit" (GU) method, 200 μL aliquots of one percent agarose in buffer are treated with a dilution series of agarase for a fixed series of times and temperatures. When the agarose is completely hydrolyzed, the release of sugar reaches a maximum as measured by the method described above. The enzyme activity is then defined as the amount of enzyme required to completely hydrolyze 200 mg of one percent SEAPLAQUE GTG (FMC Corporation) agarose in 15 minutes at 42°–47° C. in 1X TBE buffer (pH 8.3).

Figure 2:
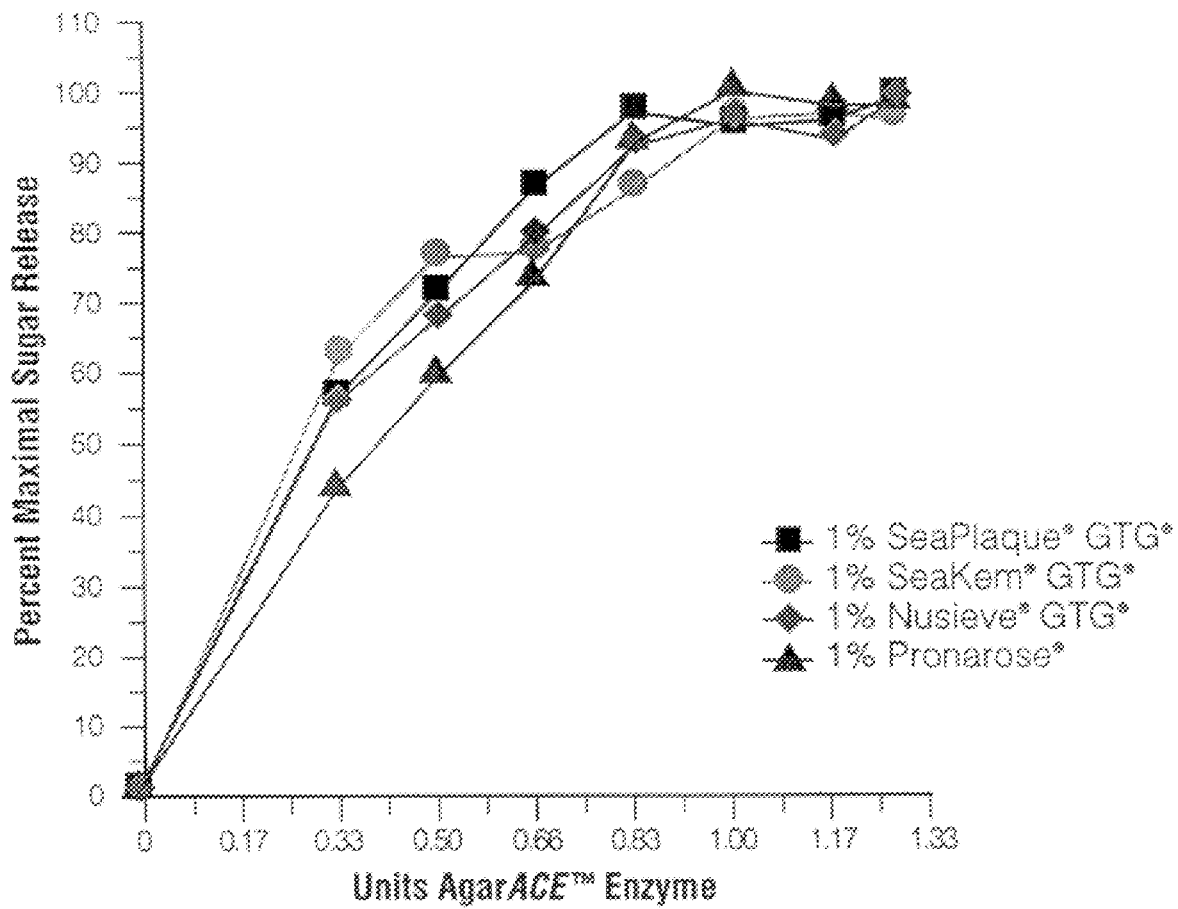
FIG. 2 is a graphic comparison of the hydrolytic activity of the 42 kD agarase of the present invention with various commercially-available agaroses.

Referring now to FIG., 2, this figure measures the ability of the 42 kD agarase isolated above to hydrolyze 1% solutions of four commercially-available agaroses: SEAPLAQUE GTG (squares), SEAKEM GTG (circles), NUSIEVE GTG (diamonds), and PRONAROSE (triangles). Aliquots of these agaroses were completely melted, and incubated for 15 minutes with different concentrations of the 42 kD enzyme. The reactions were then assayed for sugar release using the GU method. As shown in FIG. 2., the titration curves are essentially superimposable. Results shown in FIG. 2 were done with agarose in TBE buffer; however similar results, not shown, were also obtained for all agaroses in TAE buffer.

Figure 3:
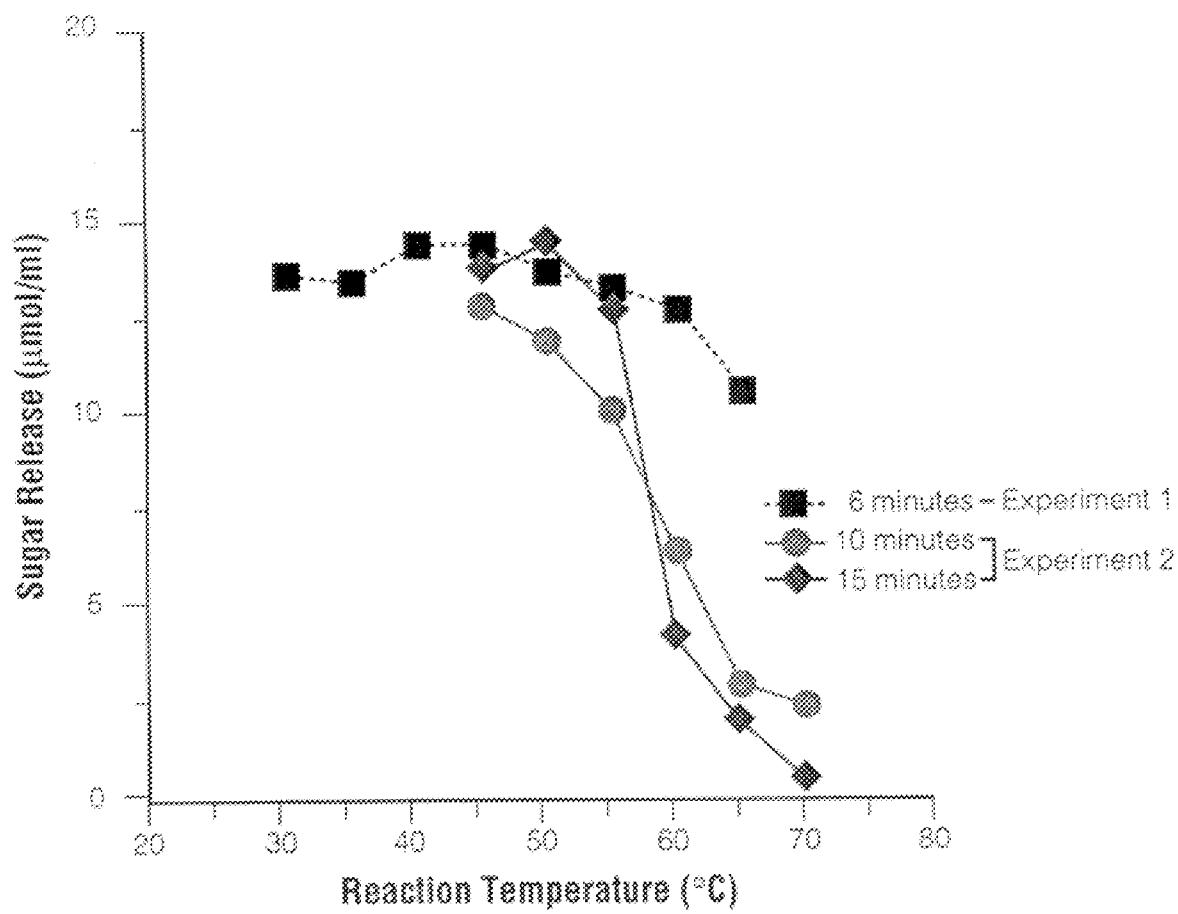
FIG. 3 is a temperature profile which shows the activity of the 42 kD agarase of the present invention as a function of temperature.

The temperature effects on the 42 kD agarase were then tested. Referring now to FIG. 3, in these experiments, the 42 kD agarase was added to molten agarose solutions which had been equilibrated at different temperatures. The enzyme was then incubated for different periods of time. The reactions were then stopped and assayed for sugar release. In Experiment 1, noted in FIG. 3, the reaction was designed to achieve incomplete hydrolysis of the substrate during the incubation period. In this experiment the 42 kD agarase was incubated with the agarose for only 6 minutes, and then the reaction stopped and assayed for sugar release. Under these conditions, maximum enzymatic activity of the 42 kD enzyme was exhibited between 40° and 50° C.

Experiment 2, also depicted in FIG. 3, allowed for more complete hydrolysis by incubating the agarase enzyme with the agarose for 10 minutes (circles) and 15 minutes (diamonds). These two experiments indicate that the activity of the 42 kD agarase remains essentially unchanged for 15 minutes at 45°–50° C. The data from Experiment 1 (squares) also indicates at 60°–70° C. the 42 kD agarase remains stable for at least short periods of time (i.e. up to 6 minutes).

To investigate the utility of the higher temperature stability of the 42 kD agarase, an experiment was performed in which aliquots of one percent agarose were melted at 70° C. and the 42 kD agarase added to the agarose at various times after the tubes were transferred to a 42° C. heating block. This experiment revealed that one unit of the 42 kD agarase enzyme hydrolyzes 200 mg of 1% agarose to completion in 15 minutes regardless of whether it is added to the solution after pre-equilibration at 42° C., or immediately after removing the tube from the high temperature heating block.

It is important to note here that other commercial agarases are rapidly inactivated at 70° C. (according to the supply literature). Consequently, when using those agarases, the agarose solution must be cooled to 40°–45° C. before enzyme addition as evidenced by their technical literature. If the solution is cooled for too short a time, the enzyme will be inactivated by the high temperature. However, if the solution is cooled for too long, the agarose begins to form the Gel I state. Since agarase cannot degrade the inner agarose helices in the Gel I fibers, incomplete digestion results.

In contrast, because the 42 kD agarase of the present invention can withstand temperatures up to 70° C. for short periods of time, it presents a distinct advantage over commercially-available agarases by permitting the digestion to proceed at a higher temperature.

Figure 4:
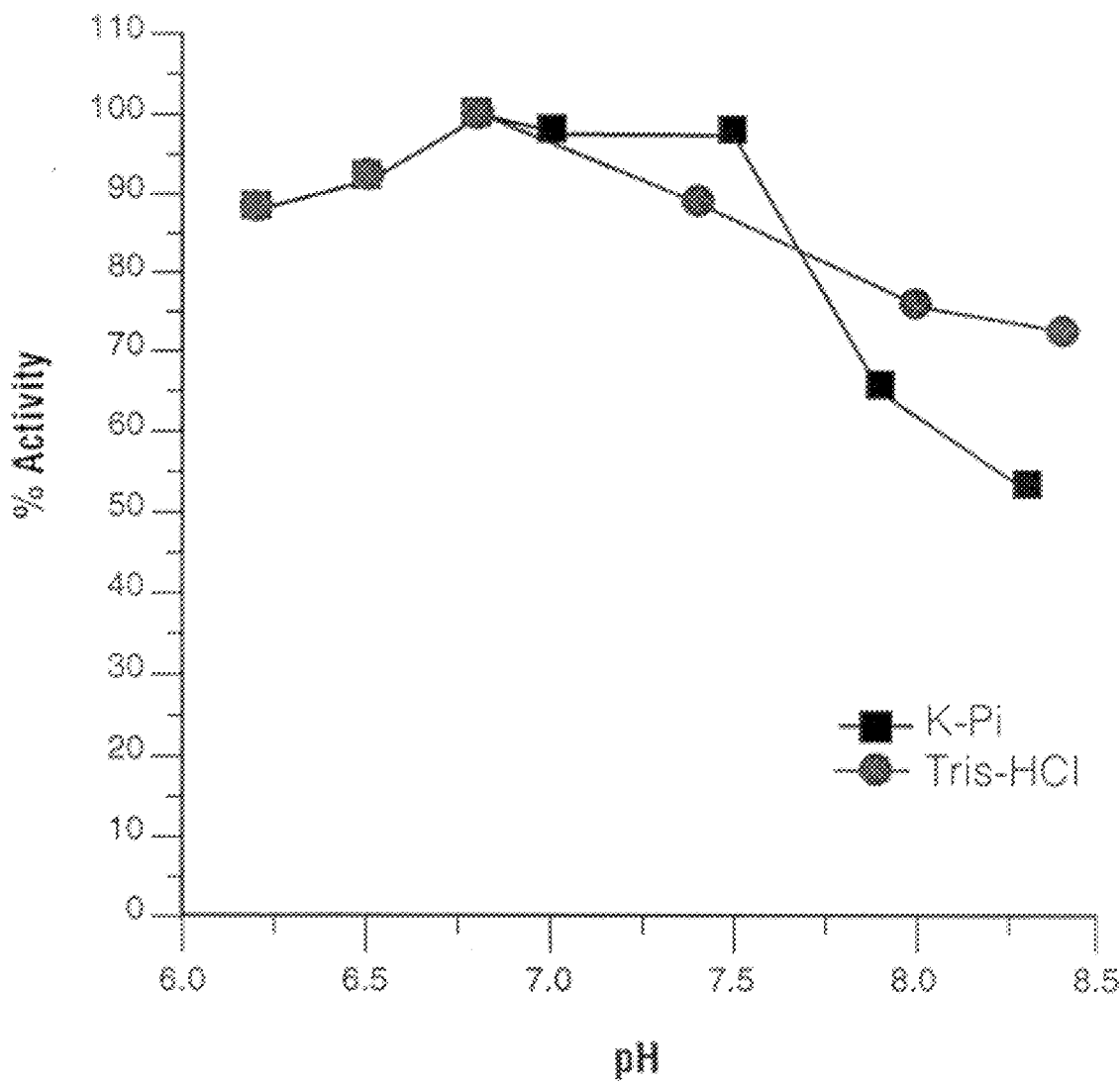
FIG. 4 is a pH profile which depict the activity of the 42 kD agarase of the present invention as a function of pH in Tris/HCl buffer (circles) and potassium phosphate buffer (squares).

FIG. 4 depicts the effect of different buffers on the ability of the 42 kD agarase to digest agarose. FIG. 4 plots the activity of the 42 kD agarase versus pH in 20 mM potassium phosphate buffer (squares) and 20 mM Tris-HCl (circles). As shown in FIG. 4, the enzyme activity drops gradually in both potassium phosphate and Tris-HCl as the pH increases beyond 7.5. In both cases, the lowest activity is observed at the high end of the pH range tested. Similar tests performed in TBE and TAE electrophoresis buffers showed that the overall activity of the 42 kD agarase enzyme is only 10–15 percent higher in those buffers than observed in Tris-HCl. Additionally, the 42 kD agarase enzyme activity is slightly higher in TAE buffer than in TBE buffer.

Because the 42 kD agarase is quite active in commonly used electrophoresis buffers (i.e., TAE and TBE) there is no need for buffer exchange nor an equilibration period in the new buffer unlike other commercially available agarases, which require buffer exchange.

Further tests were performed to assess the effect of several commonly used buffer additives on the activity of the 42 kD agarase. These test results are shown in Table I, below.

TABLE 1

Effects of Buffer Additives on 42 kD Agarase Enzyme Activity.

| Additive | Effect on enzyme activity |
| --- | --- |
| Ethidium Bromide (0.5–5 µg/ml) | None |
| Glycerol (0–50%) | None |
| DTT (0–10 mM) | None |
| NaCl (0–200 mM) | None |
| NaCl (200–500 mM) | Causes variation in the digestion rate, not recommended |
| EDTA (0–10 mM) | None |
| SDS (<0.1% w/v) | None |
| SDS (>0.3% w/v) | Inactivates enzyme |
| Glyoxal | Inactivates enzyme |
| Formaldehyde | Inactivates enzyme |

In the experiments shown in Table 1, 1% SEAPLAQUE GTG agarose in 1X TBE (ph 8.3) was melted, cooled to 45° C. and the indicated compounds were added. Enzyme activity was determined by the GU method.

Common levels of dithiothreitol (DTT), ethylenediaminetetraacetic acid (EDTA), glycerol, and ethidium bromide, do not inhibit the activity of the 42 kD agarase. Greater than 0.3% w/v sodium dodecyl sulfate inactivates the enzyme, as does glyoxal and formaldehyde, as expected.

Figure 5:
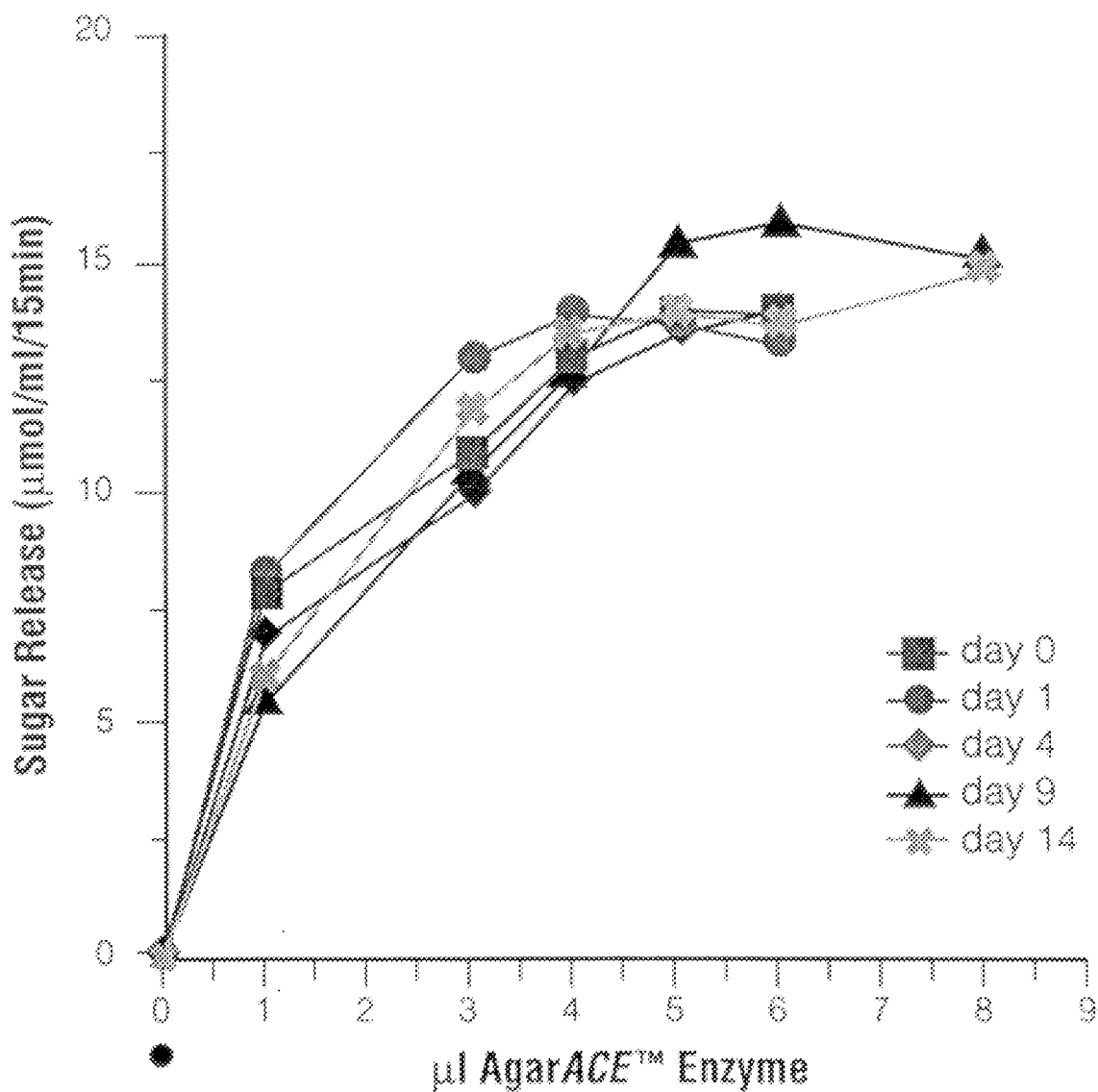
FIG. 5 is a graph depicting the effect on the activity of the 42 kD agarase of the present invention by storage at 4° C. up to 14 days. The x-axis is volume of the agarase enzyme of the present invention (AGARACE); the y-axis is activity as measured by release of sugar from agarose.
Figure 6:
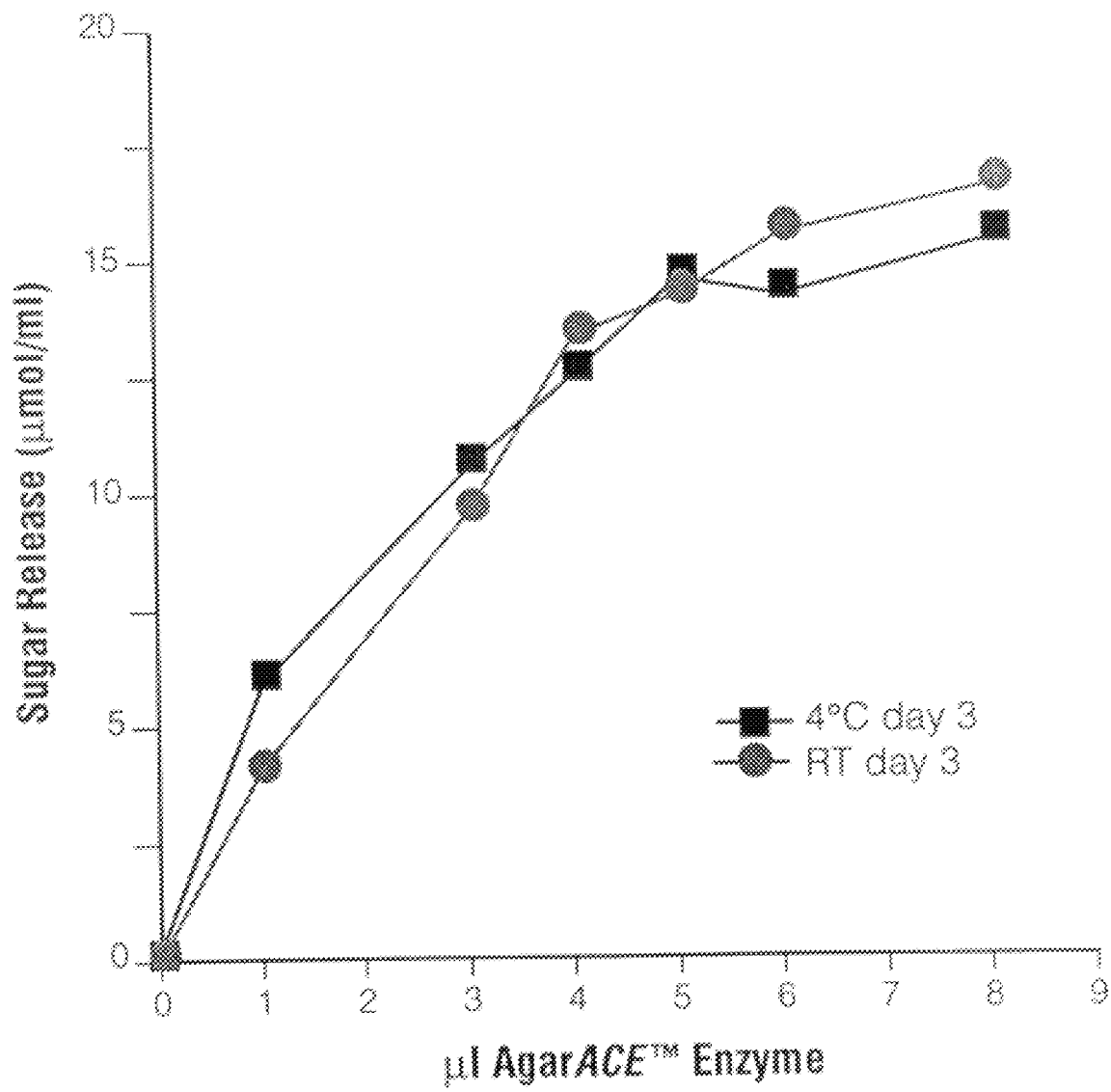
FIG. 6 is a graph comparing the activity as measured by release of sugar from agarose of the 42 kD agarase of the present invention after storage at room temperature for three days (circles) versus storage at 4° C. for three days (squares).

FIGS. 5 and 6 depict the effect of different types of storage on the activity of the 42 kD agarase. FIG. 5 shows the activity of the 42 kD agarase enzyme after storage at 4° C. As shown in FIG. 5, the activity of this enzyme remains essentially constant after 14 days of storage at 4° C. Other stability data suggests that this agarase may be stable at 4° C. for more than 3 months.

FIG. 6 shows that the 42 kD agarase enzyme stored at 3 days at room temperature has an activity which is indistinguishable from the activity of enzyme which is stored at 4° C. for the same period of time.

Additional experiments regarding the effect of freeze-thaw cycles under both fast conditions (thawed at 20° C., frozen on dry ice) and slow conditions (thawed on wet ice, frozen at −20° C.) show that under both sets of conditions, the 42 kD agarase maintains its activity for at least 10 cycles.

Stability of the 42 kD Agarase

The experiment further demonstrates the unique stability of the 42 kD agarase and relates to retention of activity under high concentrations of salt. In this experiment, 100 µl of 1% high-melting point agarose was melted at 65° C. for 30 minutes in the presence of 2.66M KI (the KI depresses the melting point of the agarose to an experimentally useful value). Next, one volume of water and 1U (by GU method) of 42 kD or other commercial agarases were added, and digestions were allowed to proceed 30 minutes at 37° C. Next, undigested agarose was precipitated with 2 volumes of ethanol and pelleted by 10 minute centrifugation in a microcentrifuge. Pellets were washed with 70% ethanol, respun, decanted, then pellets were hydrolyzed in 500 µl 0.2M HCI at 100° C. for 5 minutes. 25 µl of hydrolyzed samples were then assayed in the reducing sugar assay described earlier, and percentage precipitable agarose was calculated using an enzyme-untreated sample as the 100% point and 25 µl of 0.2M HCI as the 0% point. Whereas the 42 kD agarase from NR19 completely hydrolyzed the sample (−0.7% remaining agarose), the Pseudomonas agarase and the other commercial agarase (FMC/Epicentre) both failed to completely hydrolyze the agarose (107% and 93% remaining agarose, respectively).

Oligonucleotide Probe Construction and Cloning

To isolate the genes responsible for the production of the 42 kD and 105 kD agarases, several different techniques, each well known to those skilled in the art, may be used. For instance, the responsible genes may be present on a chromosome or a plasmid. One isolation technique involves fragmenting the genome by the use of restriction endonucleases. The resultant fragments may then be cloned into appropriate vectors in a suitable bacterial host, for instance Escherichia, Bacillus, or Salmonella. Yeast cells may also be used. Several other types of bacterial cells beyond those listed are known to the art. The resulting transformants are then screened for agarase activity. Of course, where the host does not normally produce agarase, a negative background should be obtained for the nontransformed colonies. The positive clones are then isolated.

The chromosomal elements responsible for the agarase may then be isolated by conventional techniques such as lysis of the host, precipitation of the DNA, and separation of the vector DNA, the plasmid DNA, or the viral DNA, from the chromosomal DNA of the host organism. The desired chromosomal elements are then cleaved by restriction enzymes and the desired fragments isolated by well known techniques such as gel electrophoresis or density gradient centrifugation.

An equally functional protocol is to isolate and partially sequence the agarase enzyme itself. Based on the partial amino acid sequence, DNA probes are prepared which are then used to identify the DNA fragment containing the genes of interest. The resultant fragments are then cloned and screened for the presence of the desired agarase genes.

Another method involves isolating the messenger RNA from a suitable host containing the agarase DNA fragment. By probing the MRNA with an oligonucleotide probe, the desired genetic sequence can be identified. Additionally, the mRNA of interest may be identified by using an appropriate in vitro or in vivo translation system. The isolated RNA is then used for preparing a complementary DNA via the use of a reverse transcriptase. The complementary DNA chain is then constructed using a DNA polymerase. These techniques are well known to one of skill in the art. Once the desired DNA sequence has been isolated, a large number of vectors exist which may be used for introducing the genetic sequence into a host. Such introduction can be achieved by transformation, conjugation, transduction, or transfection of the DNA into a procaryotic host such as E. coli.

Additionally, the genetic sequences which encode for the agarase enzymes may also be introduced into eukaryotic hosts. Such introduction may also be mediated by a plasmid, or may be accomplished by microinjection, electroporation, polyethylene glycol-mediated transformation of protoplasts, or by particle bombardment techniques (i.e, a gene gun). If the DNA construct is suitably competent, the DNA may be integrated into the host genome and the agarase gene successfully expressed.

Example of Cloning of the NR-19 Agarase Genes and Expression of NR19 Agarase in Heterologous Hosts A sample of the 42 kD agarose was subject to trypsin digestion and the resultant peptides separated by reversed phase HPLC under standard solvent conditions. Several peptides were collected, dried, and subject to N-terminal amino acid sequencing in an HP G1000A Protein Sequencer with Online 1090 HPLC. Three such peptides gave readable amino acid sequence as follows:

NR19-CT34: QFTHISHHSFI (SEQ. ID. NO: 1)

NR19-CT39: DWNSWYNDNR (SEQ. ID. NO: 2)

NR19-CT57: VTANYGWGDWCWNPY (SEQ. ID. NO: 3)

As noted above, the following Example is included herein solely to aid in a complete understanding of the present invention. This Example does not limit the scope of the invention disclosed and claimed herein in any fashion.

Attempts to clone the gene by colony hybridization (as described below) using oligonucleotides corresponding to the peptide sequences above were unsuccessful, due to high primer degeneracy, therefore, cloning of the 42 kD agarase gene can be accomplished by first sequencing NR19 genomic DNA using the primers:

TGGAAYWSITGGTAYAAYGAYAA (SEQ. ID. NO: 4), which corresponds to the polypeptide of SEQ. ID. NO: 2; and CCARTCICCCCAICCRTARTT (SEQ. ID. NO: 5), which corresponds to the polypeptide of SEQ. IID. NO: 3.

The fmol DNA CYCLE SEQUENCING SYSTEM (Promega) was used to sequence the DNA. 2.4 μg of NR19 genomic DNA was used for each 6 μl reaction. The cycling conditions were as follows: 99° C., 5 min. (1 cycle); 95° C., 15 seconds; 55° C., 30 seconds; 70° C., 60 seconds. Anywhere from 120 to 200 cycles were performed. The primer of SEQ. ID. NO: 5 yielded no data, while the SEQ. ID. NO: 4 primer yielded sufficient amplification products to obtain the following partial nucleotide sequence:

T G A T T G G T G C T G G N N T A A C G G C A CAGNCGNTATNTGAGACTGGGTGTCTATT GGGNAGGTCCAAAACACT (SEQ. ID. NO: 6)

N's indicate unreadable bases. Based on this partial nucleotide sequence, two complimentary oligonucleotide primers were designed:

TGCCGTTAIICCAGCACCAATCA (SEQ. ID. NO: 7) and

GGACCTICCCAATAGACACCCAGTCTCA (SEQ. ID. NO: 8).

Both primers of SEQ. ID. NOS: 7 and 8 were used to sequence NR19 genomic DNA as described above. Once translated, the sequence obtained using these primers corresponded to the known peptide sequence (SEQ. ID. NO: 2) from which the SEQ. ID. NO: 4 primer was based. This confirmed the authenticity of the new DNA sequence determined using the SEQ. ID. NO: 4 primer.

A new genomic library was made based on information obtained from above. Because the agarase gene is encoded on an approximately 6.5 Kb EcoRI fragment, as determined by Southern blot hybridization of SEQ. ID. NO: 4 to digested NR19 genomic DNA, 10 μg of NR19 genomic DNA was digested with EcoRI, the resulting fragments size fractionated on a 0.5% agarose gel, and the gel slice containing DNA in the size range of 6.5 Kb was excised. The strategy was that to encode a 42 kD protein, the gene could be as small as 1.2 kilobase (Kb), so there might be a good chance that the entire gene would be present on the 6.5 Kb fragment.

DNA was isolated out of the gel slice using WIZARD PCR Prep Resin (Promega) as described in Promega Technical Bulletin No. 118. This DNA was ligated to lambda gt10 EcoRI Arms (Promega) and packaged with PACKAGENE Lambda DNA Packaging System (Promega). Titered phage were plated out with *E. coli* C600hfl cells and the plaques were lifted onto HYBOND N circles (Amersham, Arlington Heights, Ill.) per the manufacturer's instructions. The filters were UV crosslinked with a STRATALINKER (Stratagene, La Jolla, Calif.) using the autocrosslink function. The filters were then probed with SEQ. ID. NO: 7 as follows:

The filters were prehybridized in 2X SCC, 7% SDS, 10% PEG-8000, and 250 μg/ml herring sperm DNA for 2.5 hours at 65° C. 80 pm of $^{32}$P-end labeled primer of SEQ. ID. NO: 7 was purified over a NICK COLUMN (Pharmacia Biotech, Piscataway, N.J.) before adding to the pre-hybridization solution. The hybridization proceeded for 2 hours at 55° C. The filters were then washed once at 25° C. and three times at 55° C. with 2X SCC, .1% SDS, before being exposed to X-OMAT film (Kodak) for 16 hours at –80° C.

The plaques which gave a signal were picked, eluted in SM buffer, re-plated, and re-probed as above. All of the plaques generated from each of the initially harvested plaques gave strong positive signals. A 50 ml liquid lysate was made of these lambda clones and DNA was isolated from each using WIZARD Lambda Preps DNA Purification System (Promega). Each DNA prep was sequenced with SEQ. ID. NO: 7 as described above, with the exception of using 1 μl of template DNA and cycling for 30 cycles. Identical sequences were obtained for each run. Each DNA isolate was also digested with EcoRI and each showed the same 6.5 Kb insert. The 6.5 Kb EcoRI insert from the lambda clone was subcloned into the EcoRI site of pGEM-7zf(+) (Promega) to make the plasmid pNR19-1.

The entire agarase gene was sequenced by primer walking in both directions out from the initially sequenced region. For all of the sequencing reactions, 1 μl of the NR19 lambda clone was used as the template and the fmol SEQUENCING KIT (Promega) was used. The following primers were used to sequence the 42 kD agarase gene:

CCGATTATTTGATGTTACACATCCAGA (SEQ. ID. NO: 9),

GCGGCTAGTAATAATTCGAATGGAA (SEQ. ID. NO: 10),

CAAGTATTACCTGGTCCGGCATAAG (SEQ. ID. NO: 11), and

TGGAGGATCAAATGGTACAACATGTG (SEQ. ID. NO: 12).

DNA sequencing was extended toward the C-terminus until an amber (TAG) stop codon in the same reading frame as the two sequenced peptides was encountered. DNA sequencing toward the N-terminus continued until an ochre (TAA) stop codon in the same reading frame as the two sequenced peptides was found. A methionine codon, presumably the translation initiation start site, was identified 57 base pairs downstream of the ochre stop codon. The molecular weight of the protein expressed from the ATG (methionine) codon to the amber codon would be 44.3 kD, which is in fair agreement with the known size of the enzyme from SDS-PAGE.

A putative –35 promoter region was seen 85 base pairs upstream of the ATG codon and a putative –10 promoter region was seen 57 base pairs upstream of the ATG codon. By "putative" is meant that these regions matched *E. coli* promoter consensus regions, but it remained uncertain whether Flavobacterium promoters would show homology to Escherichia promoters.

Because the 42 kD agarase enzyme is secreted into the media, it was assumed that the agarase gene would have a leader sequence. A comparison of the N-terminal region of the agarase gene to four other secreted Flavobacterium genes provided strong evidence for the presence of a leader peptide as well as a good indication that the leader cleavage site is between Asn 19 and Ala 20. With a cleavage at this site the resultant protein would then have a molecular weight of 41.95 kD, which is in excellent agreement with the known size of the agarase enzyme.

The entire gene was amplified by PCR either with or without the signal sequence and ligated into an expression vector. The PCR reaction contained 1 μg of plasmid pNR19-1, 50 pmol each of primers:

AAATTATGGCCCAAGAATGGAGTAACATT (SEQ. ID. NO: 13) and

GCTTTCTAGATAAAATCCCACCATTAATGGCATA (SEQ. ID. NO: 14) or SEQ. ID. NO: 14 and

TTCGTCATGAAAAAAAACTATT-TAATCTTTTTGCTATC (SEQ. ID. NO: 15)

in an amplification cocktail of 2 mM MgSO4, 500 μM dNTP's, and 3 units of Tli DNA Polymerase (Promega). The reaction volume was 50 μl. Thermal cycling was done in a Perkin-Elmer 480 (Serial No. 10137): 95° C., 30 sec; 65° C., 30 sec; 70° C., 90 sec; for 10 cycles. Primers and enzymes were removed from both PCR reactions with WIZARD PCR Preps DNA Purification System (Promega).

The full-length PCR product was digested with BspHI (New England Biolabs, Beverly, Mass.) and XbaI (Promega) restriction enzymes. The truncated PCR product was digested with XbaI (Promega) restriction enzyme. The PCR products were separated on a 1% agarose gel, cut out of the gel, and purified away from the agarose using PCR Preps DNA Purification System according to Promega Technical Bulletin No. 118.

The full length PCR product was ligated to JHEX23 expression vector that had been digested with NcoI and XbaI. The truncated PCR product was ligated to JHEX23 expression vector that had been digested with DraI and XbaI. This ligation places the genes directly in front of an IPTG-inducible promoter. Ligations were transformed into JM109 and the desired plasmids were screened for inserts based on their DraI digestion pattern. Both plasmids pNR19FL-23 (full length) and pNR19T-23 (truncated) were partially sequenced to confirm the promoter-gene fusion was correct. In the case pNR19T-23, the gene was truncated to remove the putative signal sequence. Thus, the expressed protein begins with an initiation methionine (MET) followed by the rest of the protein coding region, beginning with alanine in position 50 of SEQ. ID. NO: 16, which corresponds to alanine in position 1 of SEQ. ID. NO: 17. Both strains were grown in 50 ml cultures of REM with 10 μg/ml tetracycline at 25° C. The cultures were induced with 1 mM IPTG in log phase growth and sampled at about 20 hours (overnight) after induction.

Assay of Expression Results

Two ml samples of the cultures were centrifuged at 10,000 g for 15 minutes to pellet cells, then the pellets were resuspended in 1 ml of 1x PBS and cells were lysed by sonication on ice water. Lysates were clarified by centrifugation for 5 minutes at 15,000 g in a microcentrifuge, then supernatants were assayed for agarolytic activity using the transient release method described earlier. The agarolytic activity in the supernatants of the overnight samples was 0.0 and 0.19 U/ml, respectively. This established that the clone produces functional agarase, and this conclusion was supported by the observation that clones containing the pNR19T-23 plasmid created pits in the agarose plates upon which they were growing.

The full-length nucleotide sequence for the 42 kD cloned agarase gene is given in and its encoded amino acid gene product are given in SEQ. ID. NO: 16 and SEQ. ID. NO: 17, respectively.

Production of Polyclonal and Monoclonal Antibodies

150 μg of the 42 kD agarase prepared earlier were emulsified in complete Freund's adjuvant, then injected intramuscularly into a Leghorn hen. Fourteen, twenty-four, and thirty-eight days later, the hen was reinjected with 250 μl of the 42 kD agarase in incomplete Freund's adjuvant.

150 μg of the 105 kD agarase prepared earlier were emulsified in complete Freund's adjuvant, then injected intramuscularly into a Leghorn hen. Fourteen, twenty-one, and thirty-five days later, the hen was reinjected with 150 μg of 105 kD agarase in incomplete Freund's adjuvant.

Eggs from the immunized hens were collected starting the day after the first injection, then bulk IgY was prepared from the harvested eggs using the EGGSTRACT IgY Purification System (Promega Corp).

Western blots were performed using the IgY preps from the immunized hens. They revealed that the anti-42 kD antibodies reacted very well with the 42 kD agarase in both purified samples and samples of crude media. The anti-105 kD antibodies reacted with the purified 105 kD agarase and a 65 kD degradation product, and also with a large number of higher molecular weight bands in crude media samples (up to around 200 kD). Thus, it is possible that the 105 kD agarase is a fragment from a larger precursor enzyme. The Western blots also revealed that the anti-42 kD antibodies reacted slightly or not at all with the purified 105 kD agarase. Similarly, the anti-105 kD antibodies reacted slightly or not at all with the purified 42 kD agarase. This data supports the notion that the 42 kD is an independent gene product and not a fragment of the 105 kD agarase.

The present invention is not limited to the embodiments explicitly described above, but encompasses all such variations thereof which fall within the scope of the attached claims.

BIBLIOGRAPHY

U.S. Patent 5,418,156 to Stosz et al.

Aoki et al., *Eur. J. Biochem.*, (1990) Jan 26; 187(2): 461–5.

Belas, J. *Bacteriol.* (1989) Jan; 171(1): 602–5.

Bibb et al., *J. Gen. Microbiol.* (1987) Aug.; 133(Pt 8): 2089–96.

Dygert, S. et al., *Anal. Biochem.* (1965) 13: 367.

Kin, N. M. K. et al., *Carbohydrate Res.* (1972) 25: 379–385.

Morrice et al., *Eur. J. Biochem.*, (1983) Oct 3; 135(3): 553–8.

Potin et al., *Eur. J. Biochem.* (1993) June 1; 214(2): 599–607.

Sugano et al., *Appl. Environ. Microbiol.* (1993a) May; 59(5): 1549–54.

Sugano et al., *Appl. Environ. Microbiol.* (1993b) November; 59(11): 3750–6.

Sugano et al., *Biochim. Biophys. Acta.* (1994) May 17; 1218(1): 105–8.

Zuklic, Frank W. (1992) *Characterization of Bacterial Marine Isolate NR19 and the Partial Purification of its Secreted Agarase* (Masters Degree Thesis submitted to the University of South Florida).

What is claimed is:

1. A homogeneous, isolated and purified agarase from Flavobacterium sp. strain NR19, ATCC 202009, wherein the agarase has a molecular weight of about 42 kD as measured by polyacrylamide gel electrophoresis.

2. The isolated and purified agarase according to claim 1 having an isoelectric point between about 6.2 and 6.7.

3. The isolated and purified agarase according to claim 1, wherein the agarase contains an amino acid sequence as shown in SEQ. ID. NO: 17.

* * * * *